(12) United States Patent
Shiue et al.

(10) Patent No.: US 6,984,295 B2
(45) Date of Patent: Jan. 10, 2006

(54) ELECTROLYTIC CELL FOR OZONE GENERATION

(75) Inventors: Lin-Ren Shiue, Hsinchu (TW); Chia-Chann Shiue, Lungtan Shiang (TW); Hsing-Chen Chung, Hsinchu (TW); Fei-Chen Hsieh, Shi Chiu (TW); Yu-His Hsieh, Changhua (TW); Jiung-Jau Jou, Miaoli Hsien (TW)

(73) Assignee: Luxon Energy Devices Corporation, Hsinchu (TW)

( * ) Notice: Subject to any disclaimer, the term of this patent is extended or adjusted under 35 U.S.C. 154(b) by 533 days.

(21) Appl. No.: 10/068,277

(22) Filed: Feb. 6, 2002

(65) Prior Publication Data
US 2003/0146105 A1    Aug. 7, 2003

(51) Int. Cl.
C25B 1/13 (2006.01)
C25B 11/16 (2006.01)
C25B 9/04 (2006.01)

(52) U.S. Cl. ................... 204/230.8; 204/278

(58) Field of Classification Search ............... 204/242, 204/265, 252, 278, 230.8; 205/626, 756
See application file for complete search history.

(56) References Cited

U.S. PATENT DOCUMENTS

| | | | | |
|---|---|---|---|---|
| 4,541,989 A | * | 9/1985 | Foller | 422/186.07 |
| 5,426,561 A | * | 6/1995 | Yen et al. | 361/502 |
| 5,668,420 A | * | 9/1997 | Lin et al. | 310/11 |
| 5,756,054 A | * | 5/1998 | Wong et al. | 422/186.08 |

FOREIGN PATENT DOCUMENTS

JP   08-126707 A  *  5/1996
ZA      7107184 A  *  9/1973

* cited by examiner

*Primary Examiner*—Roy King
*Assistant Examiner*—Harry D. Wilkins, III
(74) *Attorney, Agent, or Firm*—J.C. Patents

(57) ABSTRACT

An electrolytic process of ozone generation using platinum-coated titanium grid as cathode, $\beta$-$PbO_2$ deposited on the grid as anode, and batteries in conjunction with supercapacitors as a DC power source is described. No membrane is required to separate the electrodes, and a neutral salt such as NaCl is used to enhance the generation of ozone gas. The electrolytic apparatus comprising a cell, the electrodes, and a bubbler can also be inserted directly in water that needs ozone treatment. As batteries can power the ozone generation, the apparatus can be disposed at point-of-use and away from the city electricity. The electrolytic apparatus can be used for sterilization of water for pharmaceutical industry, household water supply, for surface cleaning of semiconductors, meats, fish, fruits, as well as for disinfection of SPA water and personal hygiene.

12 Claims, 3 Drawing Sheets

ELECTROLYTIC CELL FOR OZONE GENERATION

BACKGROUND OF THE INVENTION

1. Field of Invention

The present invention relates to generation of ozone in an electrolytic process using batteries as power source. More particularly, the invention relates to electrolytic generation of ozone using battery and supercapacitor to provide pulse power.

2. Description of Related Art

Among all contaminants in water, the naturally occurring pathogens including enteric bacteria, viruses and protozoan cysts may induce acute illness or even death to users of the contaminated water. In comparison, the malignant effects of other pollutants such as heavy metals are generally non contagious and chronic. Depending on sanitation, water bone diseases caused by pathogenic organisms, for example, *Escherichia coli, Salmonella, vibrio cholerae, Rotavirus* and *Entamoeba histolytica,* can easily cause outbreak and become an epidemic. For destroying or screening-out biological contaminants present in a water supply, there are four major disinfection sterilization techniques commonly employed, i.e., chlorination, ozonation, micro or ultra-filtration, and ultraviolet light. In water, ozone is 150 times as powerful as chlorine and 3000 times faster than chlorine on killing microorganism cells. More importantly, ozone leaves only oxygen as residual after it takes a cell membrane apart. The destruction of microorganisms by ozone is more efficient than UV radiation just inhibiting the reproduction of microorganisms by penetrating their genetic materials. Ultra-filtration is expensive on one hand, and it retains microorganisms rather than eliminating the source of evil on the other hand. As a matter of fact, ozone has become the primary disinfectant for municipal water supply around the world.

Ozone is an allotrope of oxygen with three oxygen atoms joined together into a single molecule. Lightening produces ozone naturally by splitting oxygen molecules into single atoms, which combine with oxygen to form the short-lived triangular species. Ozone is also continuously produced in the outer layer of the atmosphere by solar UV radiation. Nevertheless, ozone can be artificially prepared by applying thousands of volts to various number of dielectric tubes comprising of aluminum lined glass tubes to convert air therein into the pungent gas. Many reports using the aforementioned method also known as "corona discharge" have been published, as in U.S. Pat. Nos. 5,503,808, 5,523,310, 5,824,274, and 6,134,806 just to cite a few, as well as numerous commercial ozone generators based on the silent discharge are on the market. Not only a very high voltage is required, but also dry air or pure oxygen is demanded for the corona discharge to generate ozone. As oxygen is split in an electric field of high voltage, so will nitrogen be simultaneously dissociated and hazardous pollutants known as $NO_x$ are formed. Removal of humidity from the input air in the discharge ozone generator is to prevent the formation of $HNO_3$ and $HNO_2$ that are corrosive to the generator. Lowering the humidity of the input air for ozone production, which will also lower the dew point of air, is not a small job. Ozone generation can be significantly improved by lowering the dew point, for example, as the dew point is lowered from −40° C. to −50° C. the ozone production efficiency is increased by 15%. However, humidity control is not the only difficulty in ozone production using corona discharge, there are other issues including $O_3$ leakage (harmful to operators and environment), $O_3$ solubility in water, and electrical safety to be taken care as well. Thus, an alternative of ozone generation with high efficiency and less restraint will be beneficial to the general acceptance of ozone for disinfection of microorganisms.

Synthesis of ozone through electrolysis has been known for over 160 years (the first report was by Schonbein; *Ann.,* Vol.50, p.616 (1840)), and the process has been patented over 30 years (for example, U.S. Pat. No. 3,256,164, Jun. 14, 1966). During electrolysis, ozone is formed on the anode of an electrolytic apparatus under the application of a low DC voltage and a high current density. Though the electrolytic process consumes more energy than that of the corona discharge (ca. 6:1), yet it has much higher current efficiency (electrolysis can reach over 50%, while discharge is about 2%), which can well compensate the energy cost. Moreover, the electrolytic process of ozone generation does not have the problems of humidity control, ozone leakage, $NO_x$ byproduct, and ozone solubility (ozone has to be dissolved in water for treatment). There are several parameters affecting the yield of electrolytic generation of ozone, they are anode, electrolyte, voltage, current density, and bath temperature. As disclosed in a publication by Foller and Tobias; "The Anodic Evolution of Ozone";*J. Electrochem. Soc.,* V01.129, No3, Mar. 1982; PP506–515, which is incorporated herein as reference, the ozone current efficiency of over 50% is attained by applying 0.5 A/cm$^2$ to β-$PbO_2$ anode in 7.3M $HPF_6$ aqueous solution at 0° C. Basically, the electrolytic generation of ozone is similar to the electrolysis of water except that a stable material with high oxygen overpotential such as β-$PbO_2$ is used as anode for ozone generation. However, $O_2$ is likewise formed on the anode (the ozone current efficiency is the concentration ratio of $O_3$ to $O_2$) and $H_2$ is formed on the cathode. Many works on electrolytic process of ozone generation dispose an ion-exchange membrane between the electrodes to prevent the mixing of $H_2$ and $O_2$ as they are formed in an electrolysis cell as disclosed in U.S. Pat. Nos. 4,416,747, 4,935,110, 5,114,549, 5,972,196, 5,997,702, and 6,143,163, which are all incorporated herein as reference. A fluorine-containing anion is included in the electrolyte of electrolytic process to improve the yield of ozone generation as in Foller's publication mentioned above and in U.S. Pat. Nos. 4,316,782, 4,541,989 and 5,154,895, the latter is also all incorporated herein as reference. Fluorine-containing anions are generally corrosive and may not be suitable for ozone generation for general use. Since the electrolytic generation of ozone is conducted on low DC voltages and high currents, and provision of the DC power coincides with the characteristics of supercapacitors, the present invention therefore employs a power module comprising batteries and supercapacitors for ozone generation. In addition, the present invention utilizes NaCl for replacing the fluorides as the electrolyte and performs the electrolysis at ambient temperature without a membrane to separate the electrodes. The table salt is a ubiquitous commodity, and the room temperature is easier to maintain than the sub-ambient temperature though the current efficiency of ozone will be somewhat impaired. A simple, affordable, and easy-to-use ozone generator can henceforth be fabricated according to the present invention for the disinfection of water for industries, families, and SPA centers, as well as for surface sterilization of meats, fish, fruits, and for personal hygiene as ozone-containing water may be used for mouth rinsing.

SUMMARY OF THE INVENTION

Ozone is a powerful and environment-friendly oxidant. It kills pathogenic microorganisms and decomposes many organic compounds that are otherwise difficult to remove from water. After ozone has done its job, it produces only $O_2$ that increases the oxygen content of water as additional benefit. Ozone treatment of water is possibly the most effective and fast technique for preparation of sterilized water. Nonetheless, ozonation should be conducted on a safe and economical manner. In accordance with an aspect of the invention there is provides an electrolytic process, whereby ozone is directly formed in water that avoids the problem of $O_3$ dissolution in water as it is encountered in the corona discharge process. To attain stability and affordablility for the electrodes, the present invention utilizes platinum-coated titanium grid as cathode, and $\beta$-$PbO_2$ deposited on the grid as anode. Comparing with other anode materials such as platinum and glassy carbon, the anode of the invention is inexpensive yet the performance is not compromised. Furthermore, the electrolytic apparatus of the invention does not require a membrane to separate the anode from the cathode, and it uses a neutral salt, for example, NaCl, KCl, $NaNO_3$ or $KNO_3$, for enhancing the generation of ozone. The apparatus comprising the electrodes and a bubbler can also be disposed directly in water to be disinfected, thus a continuous flow-through ozone treatment is attainable by placing the electrodes in the conduits of water.

Ozone generation by DC electrolysis is a process using a low DC voltage, for example, 3V~18V, and a high current that is crucial to the throughput of $O_3$ gas. Power can be provided either continuously or intermittently, the latter is by high frequency pulses, to the electrodes for generation of ozone. Pulsing powers of low voltages and high currents are best provided by supercapacitors, energy-storage devices that can be charged/discharged quickly. In accordance with another aspect of the present invention, a power module composing of supercapacitors and batteries is devised to provide energy for ozone generation. An oscillating circuit is included in the module so that the amount of power delivered to the electrodes can be controlled by varying the duty cycle of the circuit. Both primary and secondary batteries can be used to charge the supercapacitors that in-turn provide the peak currents necessary for generating ozone. Because the electrolytic apparatus of the invention is operated using batteries, it can be installed at point-of-use and away from the city electricity. Not only the use of the invention is convenient, but also it offers zero electrical hazard as it is operated by low voltages.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE PREFERRED EMBODIMENTS

It is generally known that $H_2$ will be formed on cathode and $O_2$ at anode when water is subjected to electrolysis as depicted in the following equations:

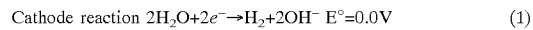
$$\text{Cathode reaction } 2H_2O + 2e^- \rightarrow H_2 + 2OH^- \quad E° = 0.0V \tag{1}$$

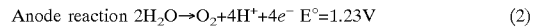
$$\text{Anode reaction } 2H_2O \rightarrow O_2 + 4H^+ + 4e^- \quad E° = 1.23V \tag{2}$$

The evolution of ozone is a higher potential anodic process as written in equation (3)

$$3H_2O \rightarrow O_3 + 6H^+ + 6e^- \quad E° = 1.6V \tag{3}$$

Figure 1:
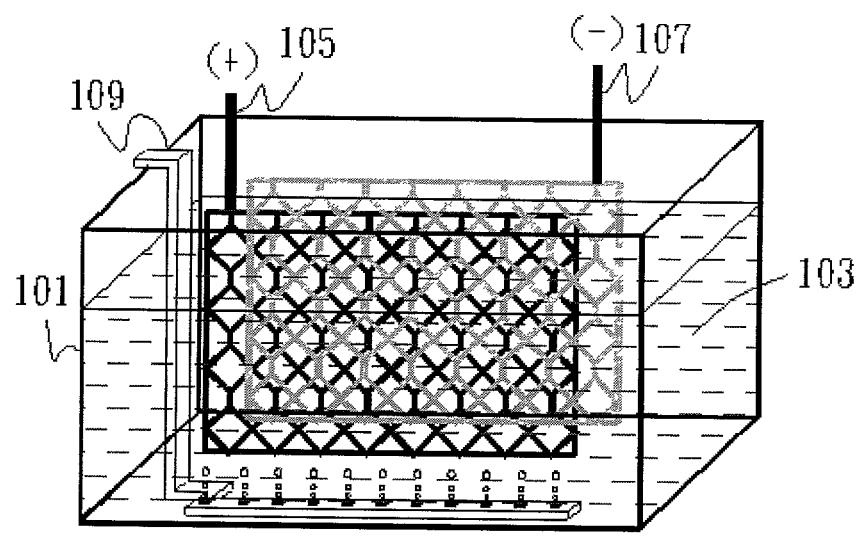
FIG. 1 illustrates a parallel arrangement of grid electrodes and electrolytic cell for generating ozone gas according to a preferred embodiment of this invention.

In order to increase the current efficiency, or the concentration ratio between $O_3$ and $O_2$, of ozone generation, high oxygen overvoltage materials must be employed. Platinum and glassy carbon are among the candidate materials as effective and stable anode for ozone evolution. Both the noble metal and the vitreous material are too costly to make a large-scale ozone generator. However, lead oxide, particularly $\beta$-$PbO_2$, is an ideal anode substitute with much lower cost than the previous two materials. As Pb is in its highest oxidation state, $PbO_2$ is stable to strong anodic polarization. The oxide is deposited anodically on a suitable substrate, for example, platinum-coated titanium (Ti/Pt), iridium oxide-coated titanium, or tin oxide-coated titanium, using an aqueous solution of lead nitrate, nitric acid, and sodium fluoride. The electrodeposition of $\beta$-$PbO_2$ is known to those skilled in the art. Based on stability (resistance to highly oxidative condition) and cost, the invention employs Ti/Pt as the substrate for anode, the plated metal is also employed as the cathode without modification. FIG. 1 shows a preferred embodiment of a parallel arrangement of grid anode 105 (Ti/Pt/$\beta$-$PbO_2$) and grid cathode 107 (Ti/Pt) in the container 101, or in an electrolytic cell. Air is bubbled through bubbler 109 into electrolyte 103 such as 10 g NaCl in 1 liter DI water to inhibit the $H_2$ evolution of equation (1). There are two functions served by air, one is to carry out ozone that is produced in the solution, the other is to provide fuel for the cathode reaction represented by equation (4), which may outproduce reaction (1) so that $H_2$ evolution is inhibited.

$$O_2 + 4H^+ + 4e^- \rightarrow 2H_2O \tag{4}$$

As disclosed U.S. Pat. No 4,316,782 issued to Foller, an air or oxygen depolarized cathode made of porous Teflon-bonded carbon solid is used to suppress the $H_2$ evolution. So long as no hydrogen is evolved to depolarize the anode and mix with ozone, there is no need of membrane to separate the electrodes. Therefore, I-R loss and cost of the electrolytic apparatus become lower due to the absence of membrane. Water is formed in reaction (4), thus periodic addition of water to the cell 101 can be avoided. Both Ti/Pt and Teflon-bonded carbon have been employed as the cathode 107 for generation of ozone in the present invention, it is found that Ti/Pt is a better cathode material than the Teflon-bonded carbon as about 30% more of ozone is generated on the former indicating no depolarization effect from hydrogen, or no hydrogen evolution.

Figure 2:
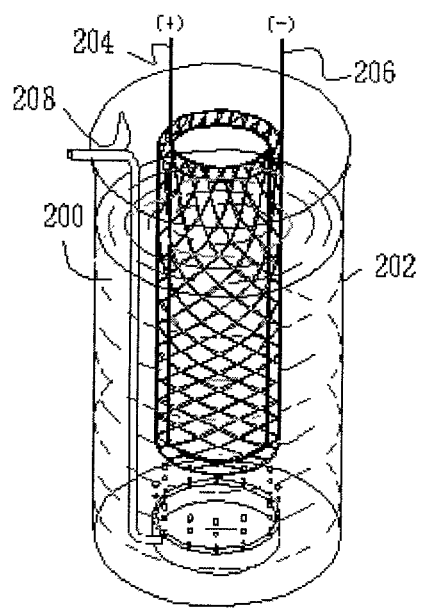
FIG. 2 illustrates a concentric arrangement of grid electrodes and electrolytic cell for generating ozone gas according to another preferred embodiment of this invention.

FIG. 2 shows another preferred embodiment of electrode arrangement in an enclosure 202 wherein anode 204 and cathode 206 are round and concentric with anode disposed at the middle. Air is also provided to cathode 206 through bubbler 208 to perform the aforementioned functions. Electrolyte 200 can be either a brine solution or water that requires ozone treatment. In other words, the electrolytic apparatus including the enclosure 202, the electrodes 204 and 206, and the bubbler 208 can be directly placed in water such as an aquarium for in-situ ozonation to maintain water in clean condition. Sufficient ozone (for example, 1~3 ppm commonly used in municipal water treatment facilities) for the disinfection of drinking water can be generated by the electrolytic apparatus by flowing the water through the electrodes. Therefore, the said electrolytic apparatus is capable of providing a continuous flow-through ozonation by placing the electrodes at selected ports of conduits of water for on-line water treatment. Electrolytic cells as depicted in FIGS. 1 and 2 can be constructed in any dimensions to fit a utensil compartment, for example, the handle of a brush, to be used for surface cleaning of medical tools and semiconductors, and for surface disinfection of meats, fish and fruits. Ozone can provide one-time fix to many dry and wet producing applications effectively and economically.

Conventionally, ozone concentration in water is determined using iodometric method wherein iodide is oxidized by ozone into iodine that then reacts with iodide to form brown triiodide complex with reaction stoichiometry as follows.

$$O_3 + 2H^+ + 3I^- \rightarrow I_3^- + H_2O + O_2 \quad (5)$$

$I_3^-$ is quantified by the universal titrant, sodium thiosulfate, using starch as indicator to form a deep blue color with triiodide. In the titration, triiodide is reduced to iodide while thiosulfate is oxidized to tetrathionate.

$$I_3^- + 2S_2O_3^{2-} \rightarrow 3I^- + S_4O_6^{2-} \quad (6)$$

As soon as the blue color fades away, the end point is reached and the titration is completed. Then the ozone concentration is calculated from the amount of thiosulfate added to reaction (6). In basic solution, $I_3^-$ disproportionates to $I^-$ and HOI. Because HOI oxidizes $S_2O_3^{2-}$ to $SO_4^{2-}$, the stoichiometry of reaction (6) changes resulting in error. Therefore, the titration of $I_3^-$ with $S_2O_3^{2-}$ should be carried out below pH 9. In the present invention the electrolytic generation of ozone using NaCl as electrolyte, pH of the solution is found to shift from 6.9 to 8.9 before and after electrolysis, such pH range is adequate for ensuring good accuracy to iodometric titration for determining the ozone concentration.

Figure 3:
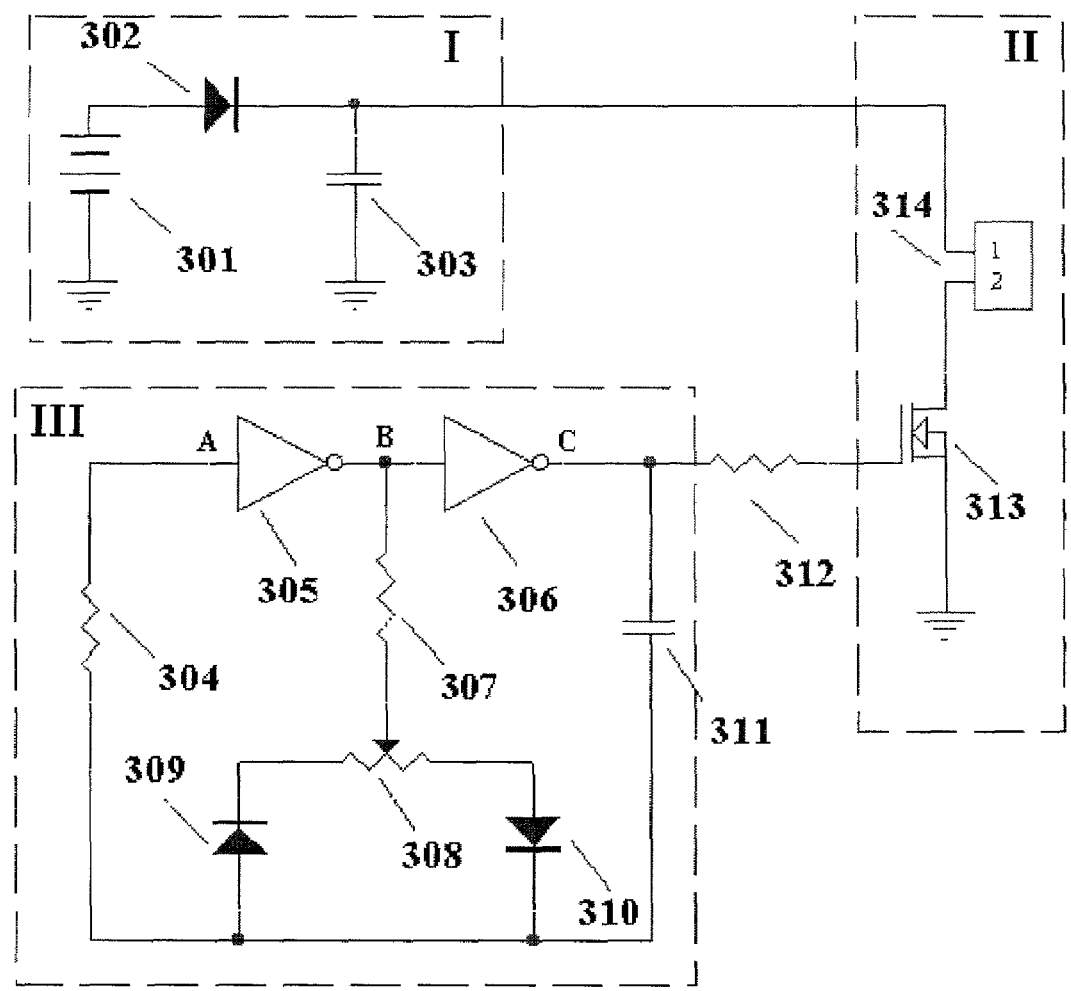
FIG. 3 illustrates a circuitry of power module comprising battery, supercapacitor, and oscillation circuit to provide pulse powers for generating ozone gas according to the preferred embodiment of this invention.

One of the advantages in ozone generation using the electrolytic process over the corona discharge is that low DC voltages, for example, 3~18 volts, can be used for the wet process. The DC voltages are much lower than that required for the corona (thousands of volts are generally employed), which means the electrolytic method is cost effective and it does not need transformer, city electricity, and prevention of electrical hazard. Though the electrolytic process may demand a higher current density than the corona discharge does to produce an equal amount of $O_3$, there is an ingenious way to meet the energy demand. It is the supercapacitors that can economically and effectively provide the required voltages and currents. On one hand supercapacitors can store energy almost to the level of batteries, and they can be charged and discharged as quickly as the conventional capacitors on the other. Hence, supercapacitors are ideal devices in a DC power source including batteries for electrolytic generation of ozone. FIG. 3 shows such a "supercapacitor/battery" hybrid-power circuitry consisting of three functional blocks, I, II and III. Block I is the power circuit with battery 301 and supercapacitor 303 connected in parallel, while diode 302 is to protect battery 301 from back charging by supercapacitor 303. The battery 301 is, for example, a dry battery, a lead-acid battery, a nickel-cadmium battery, a nickel-hydrogen battery, a lithium ion battery, a lithium polymer battery, a metal-air battery, a fuel cell, or a solar cell. Using the energy supplied by battery 301, supercapacitor 302 then provides power to load 314 or electrodes 1 and 2 (where 1 is positive electrode and 2 is negative) for $O_3$ generation. Load 314 and N-channel FET 313 form the switching circuit block II. With quick on/off switches at hundreds hertz by FET 313, pulse powers are provided to the load 314 from supercapacitor 312. The operational frequency and cycle of FET 313 is manipulated by a self-excited multi-level oscillation circuit designated as block III. Primarily the oscillator comprises high speed C-MOS NOT gates 305 and 306 that are also known as inverters, that is, their outputs are always opposite to the inputs. For example, if input A is low, then output B is high and output C is low. When output B is high, a charging current will flow from B through resistor 307 and diode 310 to charge capacitor 311. Likewise, the same charging current will flow through resistor 304, which is a current limiter to protect gate 305, to point A. As capacitor 311 is charged-up to a set voltage and point A becomes high, then point B soon turns low and point C is changed to high again.

Right on the moment of stop charging capacitor 311, it discharges to the output of gate 306, whereby the gate output is a square wave, which flows through resistor 312 serving as a current limiter to turn on FET 313. At the same instant of initiation of the discharge of capacitor 311, point A becomes low that is converted to a high for point B triggering a new cycle of charge-discharge of capacitor 311. In essence, NOT gates 305 and 306 perform as a flip-flop in self-excitation mode. The frequency of the oscillator is principally determined by the resistance of resistor 307 and capacitance of capacitor 311. Nevertheless, both resistors 304 and 308 will affect the oscillation frequency and cycle as well. The anti-parallel diodes 309 and 310 form a chopper. As the variable resistor 308 is placed to the very right end, the charging current from point B to capacitor 311 will be the largest, thus capacitor 311 is charged and discharged by the shortest time, and the square wave output from point C will have the smallest width. FET 313 will subsequently have the shortest ON time or the smallest duty ratio, and load 314 will receive the least power from supercapacitor 303. On the other hand, when the variable resistor 308 is shifted to the very left end, capacitor 311 will be charged and discharged most slowly upon the smallest charging current from point B, output C will have the widest width and FET 313 will have the largest duty ratio, load 314 will receive the largest power. In summary, FIG. 3 is a preferred embodiment that can deliver pulse powers at selected a level by varying the duty ratio of FET 313 from 1% to 99% for electrolytic generation of ozone. Therefore, the desired amount of ozone can be generated electrolytically. Followings are several experimental data cited only to demonstrate, rather than to limit, the present invention for offering a simple, economic and easy-to-use electrolytic generation of ozone for preparation of clear, fresh water.

EXAMPLE 1

Using an electrolytic cell as shown in FIG. 1, different amount of ozone was generated under various constant DC voltages. The electrolytic cell employed the following conditions:

Anode: Ti/Pt/β-PbO$_2$
Cathode: Ti/Pt
Electrode area: 10 cm$^2$
Voltage: constant voltages from a DC power supply
Electrolyte: 100 ml of 1 wt. % NaCl aqueous solution
Bath temperature: ambient
Air flow rate: 1 l/min
Electrolysis time: 1 minute The ozone concentration was determined using iodometric method. The ozone concentration together with the current recorded under each applied voltage are listed in TABLE 1.

TABLE 1

Ozone Yields under Different DC Voltages

| Applied Voltage (V) | Current Recorded (A) | O$_3$ Yield (mg) |
|---|---|---|
| 6 | 0.28 | 0.79 |
| 10 | 0.67 | 1.68 |
| 12 | 0.90 | 1.98 |
| 16 | 1.30 | 2.13 |
| 18 | 1.64 | 2.18 |
| 20 | 1.60 | 2.00 |
| 24 | 3.10 | 1.50 |

Figure 4A:
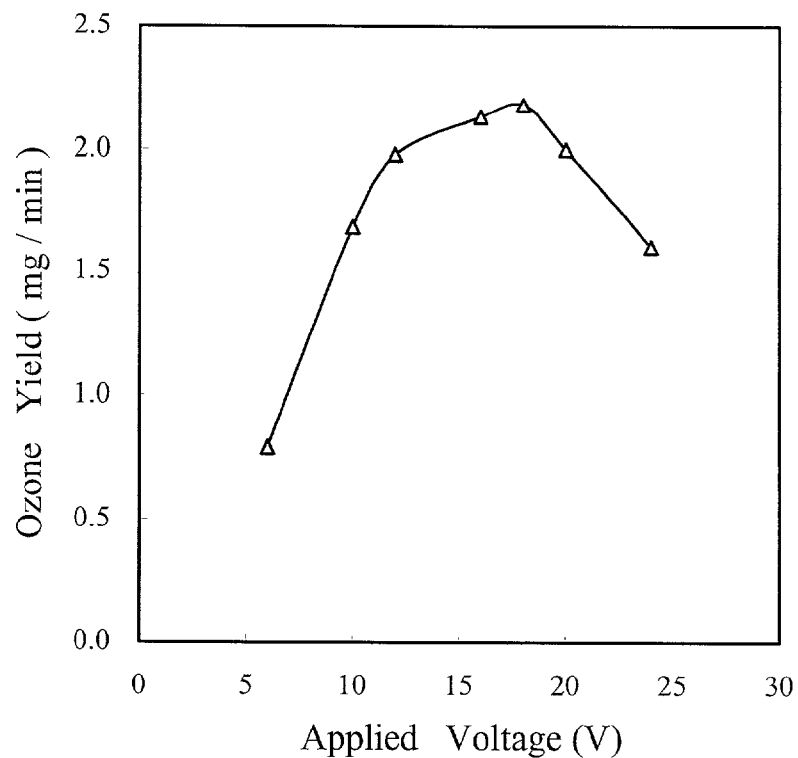
FIG. 4A plots the relationship between ozone yield and applied voltage according to the preferred embodiment of this invention.

When the ozone yield is plotted against the applied voltage, FIG. 4A is resulted. As seen in the drawing, the ozone generation reaches maximum around 18 volts in the above electrolysis conditions.

EXAMPLE 2

Same electrolytic apparatus and same electrolysis conditions as example 1, different ozone concentration was generated potentiostatically using 24 DC volts and different electrolytes. The outcome is as follows:

| Electrolytes | Current (A) | O$_3$ Yield (mg) |
|---|---|---|
| 10 wt. % NaCl | 3.12 | 2.79 |
| 30% NaCl | 6.34 | 1.98 |
| 10 wt. % KNO$_3$ | 1.98 | 0.04 |
| 10 wt. % NaBF$_4$ | 0.54 | 0.03 |

EXAMPLE 3

Same electrolytic apparatus as Examp1, except the electrolyte, a 10 wt. % NaCl aqueous solution, was flowed through the electrodes in two flow rates. Ozone was generated and cumulated in 100-ml of effluent collected. The ozone concentration at each flow rate was determined using iodometric titration.

| Flow rate (ml/min) | Current (A) | O$_3$ Yield (mg) |
|---|---|---|
| 30 | 0.98 | 2.57 |
| 100 | 0.74 | 1.67 |

It is obvious that a continuous on-line ozone treatment for disinfection of water is feasible using the present invention.

EXAMPLE 4

Same electrolytic apparatus as Example 1, except a 12V lead-acid battery and supercapacitors were employed as power source as depicted in FIG. 3 for electrolytic generation of ozone. TABLE 2 shows the ozone yields under different duty ratio.

TABLE 2

Ozone Yields and Duty Ratio

| Duty Ratio (%) | O$_3$ Yield (mg) |
|---|---|
| 25 | 0.88 |
| 50 | 1.51 |
| 75 | 2.26 |
| 99 | 2.48 |

Figure 4B:
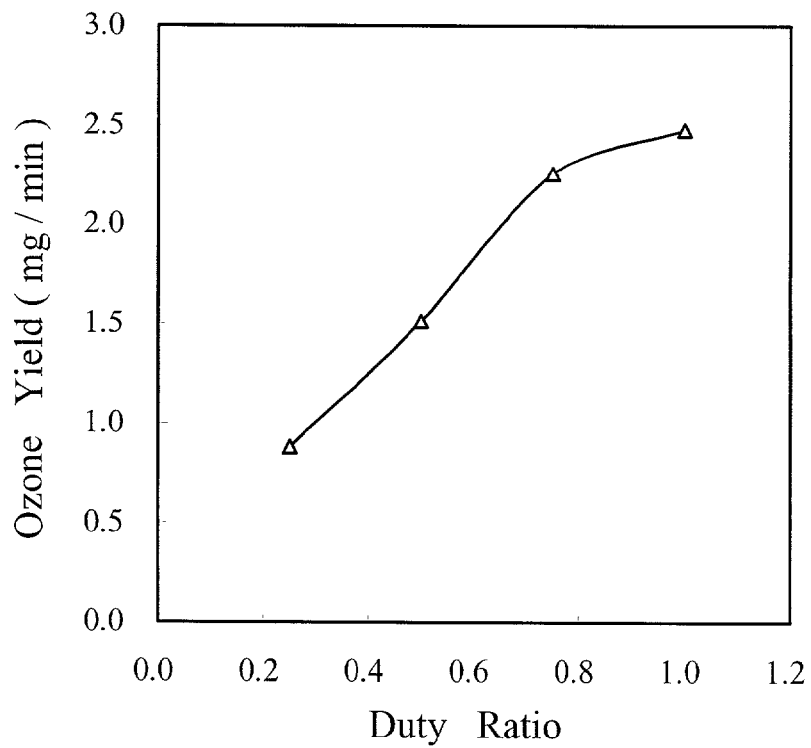
FIG. 4B plots the relationship between ozone yield and duty ratio according to the preferred embodiment of this invention.

When the ozone yield is plotted against duty ratio, FIG. 4B is resulted. As expected, more ozone is generated at larger duty ratio for more energy is provided to electrolysis. This is convenient for applications that do not require high ozone concentration. Custom-made level of ozone for water treatment is therefore easily attainable using the control of duty ratio. From the above examples, the present invention is evidently feasible for generating ozone electrolytically for water treatments.

It will be apparent to those skilled in the art that various modifications and variations can be made to the structure of the present invention without departing from the scope or spirit of the invention. In view of the foregoing, it is intended that the present invention covers modifications and variations of this invention provided they fall within the scope of the following claims and their equivalents.

What is claimed is:

1. An electrolytic cell for ozone generation, comprising: two grid electrodes immersed in an electrolyte, the two grid electrodes being powered by a DC power source continuously or intermittently, wherein the DC power source comprises an oscillator containing a circuitry comprising a power circuit, a switching circuit and self-excited multi-level oscillation circuit;
the electrolyte comprises at least one neutral salt;
a first electrode of the two grid electrodes is an anode, wherein a material of the anode comprises titanium coated with another material selected from the group consisting of platinum, iridium oxide and tin oxide, and a layer of β-PbO$_2$ is coated on the anode, and
a second electrode of the two grid electrodes is a cathode, wherein a material of the cathode comprises titanium coated with another material selected from the group consisting of platinum iridium oxide and tin oxide.

2. An electrolytic cell for ozone generation of claim 1, wherein the neutral salt comprises at least one salt selected from the group consisting of NaCl, KCl, NaNO$_3$, and KNO$_3$.

3. An electrolytic cell for ozone generation of claim 1, wherein the DC power source comprises a battery.

4. An electrolytic cell for ozone generation of claim 3, wherein the battery is selected from a group consisting of dry battery, lead-acid battery, nickel-cadmium battery, nickel-hydrogen battery, lithium ion battery, lithium polymer battery, metal-air battery, fuel cell, and solar cell.

5. An electrolytic cell for ozone generation of claim 1, wherein the DC power source further comprises a battery and a supercapacitor.

6. An electrolytic cell for ozone generation of claim 5, wherein the battery is selected from a group consisting of dry battery, lead-acid battery, nickel-cadmium battery, nickel-hydrogen battery, lithium ion battery, lithium polymer battery, metal-air battery, fuel cell, and solar cell.

7. An electrolytic cell for ozone generation of claim 5, wherein the oscillator comprises a self-excitation multi-level oscillator.

8. An electrolytic cell for ozone generation of claim 5, wherein a yield of ozone generation is controlled by varying a duty ratio of the circuitry of the DC power source.

9. An electrolytic cell for ozone generation of claim 5, further comprising a bubbler for supplying bubbles into the electrolyte.

10. An electrolytic cell for ozone generation of claim 1, further comprising a bubbler for supplying bubbles into the electrolyte.

11. An electrolytic cell for ozone generation of claim 1, which has a temperature including room temperature.

12. An electrolytic cell for ozone generation of claim 1, wherein the current used in the electrolytic cell is between 0.28–3.10 A.

* * * * *